United States Patent [19]

Stoll et al.

[11] Patent Number: 5,245,062

[45] Date of Patent: Sep. 14, 1993

[54] PROCESS FOR THE PRODUCTION OF KETONE COMPOUNDS

[75] Inventors: Gerhard Stoll, Korschenbroich; Elke Grundt, Hilden, both of Fed. Rep. of Germany

[73] Assignee: Henkel Kommanditgesellschaft auf Aktien, Duesseldorf-Holthausen, Fed. Rep. of Germany

[21] Appl. No.: 910,326

[22] PCT Filed: Jan. 10, 1991

[86] PCT No.: PCT/EP91/00025

§ 371 Date: Jul. 20, 1992

§ 102(e) Date: Jul. 20, 1992

[87] PCT Pub. No.: WO91/10636

PCT Pub. Date: Jul. 25, 1991

[30] Foreign Application Priority Data

Jan. 18, 1990 [DE] Fed. Rep. of Germany ....... 4001316

[51] Int. Cl.$^5$ ............... C07C 51/373; C07C 69/66; C07C 45/67

[52] U.S. Cl. ................. 554/149; 560/174; 568/322; 568/386

[58] Field of Search ........... 554/149; 568/386, 322; 560/174

[56] References Cited

U.S. PATENT DOCUMENTS

| | | | |
|---|---|---|---|
| 2,485,160 | 7/1992 | Niederhauser et al. | 260/348 |
| 2,933,534 | 4/1960 | Stansbury et al. | 568/322 |
| 3,736,319 | 5/1973 | Martel et al. | 560/174 |
| 4,035,395 | 7/1977 | Stetter et al. | 560/174 |
| 4,734,529 | 3/1988 | Berg et al. | 568/310 |
| 5,032,323 | 7/1991 | Virnig | 560/174 |

FOREIGN PATENT DOCUMENTS

| | | |
|---|---|---|
| 0220792 | 5/1987 | European Pat. Off. |
| 3334600 | 4/1985 | Fed. Rep. of Germany |
| 3601380 | 7/1987 | Fed. Rep. of Germany |
| 0061328 | 5/1981 | Japan |

OTHER PUBLICATIONS

Chemical Communications, D. Bethell et al., vol. 4, 1968, pp. 227–229.
Journal of the American Chemical Society, B. Rickborn et al., vol. 90, 1968, pp. 4193/4194.
Organic Synthesis, 33, 84–87, Dobsen et al., 1953.
J. American Chemical Society, 77, pp. 3070–3075, 1955.
J. American Chemical Society, 5983 (1955).
J. American Oil Chem. Soc., 79 6283 (1957).

Primary Examiner—José G. Dees
Assistant Examiner—Dwayne C. Jones
Attorney, Agent, or Firm—Ernest G. Szoke; Wayne C. Jaeschke; John E. Drach

[57] ABSTRACT

Ketone compounds are obtained by rearrangement of epoxides in the presence of iodide ions providing quaternary ammonium and phosphonium salts, optionally in admixture with alkali metal or alkaline earth metal iodides, are used as the rearrangement catalysts.

8 Claims, No Drawings

PROCESS FOR THE PRODUCTION OF KETONE COMPOUNDS

BACKGROUND OF THE INVENTION

1. Field of the Invention

This invention relates to a process for the production of ketone compounds by rearrangement of epoxides in the presence of iodide ions, in which quaternary ammonium or phosphonium salts, optionally in admixture with alkali metal or alkaline earth metal iodides, are used as the rearrangement catalysts.

2. Statement of Related Art

Ketone compounds having long, optionally substituted alkyl or aryl radicals are valuable intermediate products for the chemical industry and are used, for example, as foam inhibitors or in the production of PVC co-stabilizers.

Although there are a number of methods for the production of these compounds, they are all attended by the disadvantage of considerable preparative effort. Thus, fatty ketones can be obtained, for example, by pyrolysis of magnesium salts at high temperatures [Organic Synthesis, 33, 84] or by rearrangement of the epoxides in the presence of magnesium halide etherate [J. Am. Chem. Soc., 77, 3070, 5083 (1955), J. Am. Oil. Chem. Soc., 79, 6283 (1957)].

German patent application DE 36 01 380 A1 describes a simpler process in which epoxidized fatty acid esters are rearranged into the corresponding oxo compounds in the presence of sodium iodide and polyethylene glycols at 160° to 200° C. However, this process has the disadvantage that it involves the use of a solubilizer and, in addition, gives poor rearrangement yields.

The object of the present invention is to develop a process for the production of ketone compounds which is not attended by any of the described disadvantages.

The present invention relates to a process for the production of ketone compounds by rearrangement of epoxides in the presence of iodide ions, in which quaternary ammonium or phosphonium salts, optionally in admixture with alkali metal or alkaline earth metal iodides, are used as the rearrangement catalysts.

In this way, epoxides can be converted into the corresponding ketone compounds with high yields in the absence of solubilizers.

In the context of the invention, the term "epoxide" is understood to encompass compounds which contain at least one oxirane group and at least six carbon atoms, at least one of the four substituents of the oxirane group being a hydrogen atom.

Compounds which can be rearranged into ketone compounds by the process according to the invention belong to the following classes:

a) Epoxides of aliphatic or cycloaliphatic monoolefins containing 6 to 30 carbon atoms, such as for example hex-1-ene, cyclohexene, oct-1-ene, cyclooctene, dec-1-ene, dodec-1-ene, cyclododecene, tetradec-1-ene, hexadec-1-ene, octadec-1-ene, oct-2-ene, oct-3-ene, oct-4-ene, dec-5-ene, dodec-6-ene, tetradec-7-ene or octadec-9-ene. Olefins containing 12 to 18 carbon atoms are preferably used as starting materials.

b) Epoxides of esters of unsaturated fatty acids containing 11 to 22 carbon atoms and 1, 2 or 3 double bonds with linear or branched, aliphatic, saturated or unsaturated alcohols containing 1 to 22 carbon atoms and 0, 1, 2 or 3 double bonds, araliphatic alcohols containing 7 to 15 carbon atoms or phenols.

DESCRIPTION OF THE INVENTION

Examples of typical unsaturated fatty acids are undecylenic acid, palmitoleic acid, elaidic acid, linoleic acid, linolenic acid, chaulmoogric acid or erucic acid. Oleic acid or petroselic acid esters are preferably used as starting materials.

Examples of typical saturated alcohols are ethanol, 1-propanol, 2-propanol, caproic alcohol, caprylic alcohol, capric alcohol, lauryl alcohol, myristyl alcohol, cetyl alcohol, stearyl alcohol or behenyl alcohol. Alcohols containing 1 to 8 carbon atoms are preferably used as starting materials, methyl, butyl and 2-ethylhexyl esters being particularly preferred.

Examples of typical unsaturated alcohols are allyl alcohol, undecenyl alcohol, palmitoleyl alcohol, elaidyl alcohol, linoleyl alcohol, linolenyl alcohol or erucyl alcohol. Oleyl or petroselinyl esters are preferably used as starting materials.

Esters of unsaturated fatty acids with unsaturated fatty alcohols may contain the oxirane group in the fatty acid component and/or the alcohol component. If the fatty acid component and/or alcohol component are polyunsaturated, they may also contain more than one oxirane group.

c) Epoxides of esters of unsaturated fatty acids with polyols, for example ethylene glycol, diethylene glycol, triethylene glycol, propylene glycol, diglycerol, triglycerol, trimethylol propane, pentaerythritol or sorbitan. However, unsaturated fatty acid glycerol esters are preferably used as starting materials.

Fatty acid glycerol esters are understood to be the mono-, di- and triesters and mixtures thereof, as obtained for example where production is carried out by esterification of 1 mol glycerol with 1 to 3 mol unsaturated fatty acid or in the transesterification of unsaturated triglycerides with 0.5 to 2 mol glycerol. It is particularly preferred to rearrange epoxides of unsaturated fatty glycerol esters which are derived from fatty acids containing 16 to 24 carbon atoms and 1 to 5 double bonds, for example from palmitoleic acid, oleic acid, elaidic acid, petroselic acid, erucic acid, linoleic acid, linolenic acid, chaulmoogric acid, arachidonic acid or clupanodonic acid. By virtue of their ready availability, it is preferred to start out from technical fatty acid glycerol ester mixtures of which the fatty acid component contains more than 50% by weight oleic acid or linoleic acid.

The fatty acid glycerol esters may be of synthetic or natural origin. Preferred esters are those obtained from soybean oil, cottonseed oil, ground nut oil, olive oil, linseed oil, lard oil, meadow foam oil, chaulmoogra oil, lard or fish oil, rapeseed oil rich in oleic acid, sunflower oil rich in oleic acid or coriander oil being particularly preferred. It is also possible specifically to use native fatty acid glycerol esters, of which most, i.e. more than 50% by weight, but not all of the fatty acid component consists of the unsaturated fatty acids mentioned, and technical mixtures of various unsaturated or substantially unsaturated fatty acid glycerol esters with one another providing the content of unsaturated fatty acids in the mixtures is again more than 50% by weight.

d) Epoxides of esters of saturated aliphatic carboxylic acids containing 1 to 22 carbon atoms with aliphatic unsaturated alcohols containing 1 to 22 carbon atoms or 1, 2 or 3 double bonds.

Examples of typical saturated aliphatic carboxylic acids are formic acid, propionic acid, butyric acid, valeric acid, caproic acid, caprylic acid, capric acid, lauric acid, myristic acid, palmitic acid or behenic acid. Acetic acid or stearic acid esters are preferably used as starting materials.

Examples of typical unsaturated alcohols are allyl alcohol, undecenyl alcohol, palmitoleyl alcohol, elaidyl alcohol, linoleyl alcohol, linolenyl alcohol or erucyl alcohol. Oleyl or petroselinyl esters are preferably used as starting materials.

e) Epoxides of alkenyl ethers and alkenyl (poly)alkylene glycol ethers containing an alkenyl radical with 11 to 12 carbon atoms and 1, 2 or 3 double bonds and another linear or branched alkyl or alkenyl radical containing 1 to 22 carbon atoms, an aralkyl radical containing 7 to 15 carbon atoms or a phenyl radical. The polyalkylene glycol ethers may be polyethylene glycol or polypropylene glycol ethers and may contain 1 to 10 and preferably 1 to 5 alkylene glycol units.

Alkenyl ethers of this type may be obtained, for example, by Williamson's ether synthesis, in which an unsaturated fatty alcohol or an alkylene oxide adduct thereof is reacted with corresponding alkyl, alkenyl, aralkyl or aryl halide.

Typical examples of alkenyl ethers are diundecenyl ether, dioleyl ether, dielaidyl ether, dipetroselinyl ether, oleylmethyl ether, oleylbutyl ether, oleylbenzyl ether, oleyl alcohol-2EO-methyl ether, oleyl alcohol-4EO-butyl ether or oleyl alcohol-5EO-benzyl ether.

Epoxides of the type mentioned are obtained by epoxidation of unsaturated compounds, for example by the method described in DE 857 364, by reaction with peracetic acid in the presence of acidic catalysts or with performic acid formed in situ from formic acid and hydrogen in accordance with US-PS 2,485,160.

In the quaternary ammonium or phosphonium salts used as rearrangement catalysts, suitable substituents are linear and/or branched alkyl radicals containing 1 to 22 carbon atoms, such as for example ethyl, propyl, 2-ethylhexyl, lauryl or cetyl radicals, aralkyl radicals containing 7 to 15 carbon atoms, such as for example benzyl radicals, and aryl radicals containing 6 to 12 carbon atoms. Methyl-, butyl-, phenyl- and/or stearyl-substituted ammonium or phosphonium salts are preferably used as the rearrangement catalysts.

The quaternary ammonium or phosphonium salts may contain the alkyl, aralkyl or aryl radicals in any substitution pattern. However, it has proved to be of particular advantage to use ammonium or phosphonium salts containing four substituents of the same type or two short-chain substituents and two relatively long-chain substituents. Examples of such salts are tetrabutyl phosphonium or di-methyl distearyl ammonium salts. They may either be used as such or may be produced in situ from tertiary amines or phosphines and alkyl or aryl halides.

The quaternary ammonium and phosphonium salts may be present as halides or pseudohalides, more particularly as chlorides and, preferably, iodides.

By virtue of their ready availability, their high catalytic activity, their chemical stability and their ready removability, tetrabutyl and tetraphenyl phosphonium iodide are particularly preferred for the rearrangement of epoxides into ketone compounds.

The concentration of the quaternary ammonium or phosphonium salts may be from 0.05 to 10 mol-%. However, yields of more than 70%, based on the epoxide used, and short reaction times are only obtained where the salts are used in concentrations above 0.5 mol-%, concentrations of more than 5 mol-% result in the shortening of the reaction times to only a negligible extent.

In one preferred embodiment of the invention, the quaternary ammonium or phosphonium salts are used in the form of their iodides. However, in the presence of alkali metal or alkaline earth metal iodides, particularly sodium iodide, the corresponding chlorides or bromides may also be used.

The alkali metal or alkaline earth metal iodide may be used in concentrations of 0.1 to 8 mol-% and preferably 0.1 to 5 mol-%, based on the epoxide, while the molar ratio of quaternary ammonium or phosphonium salt to alkali metal or alkaline earth metal iodide is from 2:1 to 1:5.

In another preferred embodiment of the invention, mixtures of dimethyl distearyl ammonium chloride and sodium iodide are used by virtue of their ready availability and high activity.

To rearrange the epoxides into ketone compounds, the starting materials and the catalyst or catalyst mixture are stirred for 120 to 600 minutes at 160° to 230° C. and preferably at 180° to 200° C. in an inert gas atmosphere. If the ketone compounds obtained by rearrangement can be distilled, the rearrangement product may be recovered by distillation, optionally in vacuo. The distillation residue containing the ammonium or phosphonium salt and, optionally, sodium iodide is catalytically active and, in these cases, may be returned to the rearrangement without working up. If the rearrangement product cannot be distilled, it is sufficient to remove the catalyst by washing out with hot water.

In many cases, the epoxide does not have to be completely rearranged into the corresponding ketone compounds. For example, it is sufficient to prepare mixtures containing only 20 to 50% by weight of the rearrangement product, based on the epoxide. Technical mixtures such as these can be prepared with continuous monitoring of the epoxide oxygen content of the reaction mixture until the desired residual epoxide oxygen content has been reached.

The invention is illustrated by the following Examples.

EXAMPLES

| Starting materials (educts, E) | | |
|---|---|---|
| E2 Epoxidized technical oleic acid methyl ester | | |
| Epoxide oxygen content (EpOV): | 4.95 | % by weight |
| 9,10-epoxystearic acid methyl ester content: | 70 | % by weight |
| Saponification value (SV) | 187.8 | |
| E2 Epoxidized n-C$_{13/14}$ olefin mixture | | |
| Epoxide oxygen content (EpOV): | 6.74 | % by weight |
| Epoxidized n-C$_{13}$-olefin content: | 58 | % by weight |
| Epoxidized n-C$_{14}$-olefin content: | 40 | % by weight |
| E3 Epoxidized sunflower oil rich in oleic acid | | |
| Epoxide oxygen content (EpOV): | 4.55 | % by weight |
| Oleic acid content before epoxidation: | 80 | % by weight |
| Saponification value (SV): | 183.0 | |
| Iodine value (IV): | 2.1 | |
| Acid value (AV): | 3.4 | |
| E4 Epoxidized soybean oil | | |
| Epoxide oxygen content (EpOV): | 6.78 | % by weight |
| Saponification value (SV): | 181.8 | |
| Iodine value (IV): | 3.4 | |
| Acid value (AV): | 0.4 | |
| E5 1,2-epoxyoctadecane | | |
| Epoxide oxygen content (EpOV): | 5.42 | % by weight |

| Tetrasubstituted ammonium or phosphonium salts (A) | |
| --- | --- |
| A1 Tetrabutyl phosphonium iodide | M = 386, Aldrich |
| A2 Tetrabutyl phosphonium bromide | M = 339, Aldrich |
| A3 Dimethyl distearyl ammonium chloride | M = 588, Dehyquart ® DAM, Henkel |

REARRANGEMENT OF EPOXIDES:

EXAMPLES 1-5

General procedure for the rearrangement of epoxidized oleic acid methyl ester 500 g (1.55 mol) epoxidized oleic acid methyl ester (E1) were introduced into a three-necked flask equipped with a stirrer, reflux condenser and internal thermometer, followed by the addition of 1 to 5 mol-% (based on the epoxide) of a tetraalkyl ammonium or phosphonium salt (A1, A2, A3) and, optionally, 1 to 5 mol-% (based on the epoxide) of sodium iodide. The reaction mixture was stirred under nitrogen over a period t of 165 to 585 minutes at a temperature T of 180° to 200° C. A mixture of 9- and 10-ketostearic acid methyl ester in the form of a yellow crystalline solid was obtained as the rearrangement product by distillation in vacuo (0.04 to 0.02 mbar, sump temperature 200° C.) together with a distillation residue containing the transesterification catalyst. The characteristic data of the product are shown in Table 1.

EXAMPLE 6

Example 1 was repeated. The distillation residue (112.8 g) of Example 1 was used as the catalyst. The characteristic data of the product are shown in Table 1.

EXAMPLE 7

Rearrangement of epoxidized n-olefins 500 g (2.1 mol) of an epoxidized mixture of n-olefins (E2) were introduced into a three-necked flask equipped with a stirrer, reflux condenser and internal thermometer, followed by the addition of 2 mol-% (based on the epoxide) of tetrabutyl phosphonium bromide (A1) and 1 mol-% (based on the epoxide) of sodium iodide. The reaction mixture was stirred under nitrogen for 420 minutes at 180° C. After cooling and washing twice with 250 ml water at 30° C., the organic phase was distilled off in vacuo (0.04 to 0.02 mbar, sump temperature 80° to 130° C.). The rearrangement product was obtained in the form of a pale yellow, clear liquid. The characteristic data of the product are shown in Table 1.

EXAMPLES 8-10

Partial rearrangement of epoxidized fatty acid glycerol esters 1000 g (2.81 mol) of an epoxidized fatty acid glycerol ester (E3, E4) were introduced into a three-necked flask equipped with a stirrer, reflux condenser and internal thermometer, followed by the addition of 0.64 to 1.2 mol-% (based on the epoxide) of a tetraalkyl ammonium or phosphonium salt (A1, A3) and, optionally, 2.3 mol-% (based on the epoxide) of sodium iodide. The reaction mixture was stirred under nitrogen over a period t of 270 to 540 minutes at a temperature T of 200.C. After cooling and washing four times with hot water at 60° C. and drying of the product in vacuo (0.02 mbar, 90° C.), the partial rearrangement products were obtained in the form of brown solids. The characteristic data of the products are shown in Table 1.

EXAMPLE 11

Rearrangement of 1,2-epoxyoctadecane 1000 g (3.4 mol) 1,2-epoxyoctadecane (E5) were introduced into a three-necked flask equipped with a stirrer, reflux condenser and internal thermometer, followed by the addition of 1 mol-% (based on the epoxide) of dimethyl distearyl ammonium chloride (A3) and 2 mol-% (based on the epoxide) sodium iodide. The reaction mixture was stirred under nitrogen for 510 minutes at 200° C. After fractional distillation in vacuo (0.08 to 0.1 mbar, sump temperature 136° to 153° C.), the rearrangement product was obtained in the form of a colorless solid. The characteristic data of the product are shown in Table 1.

TABLE 1

Characteristic data of the rearrangement products

| Ex. | E | A | A mol-% | NaI mol-% | T °C. | t mins. | Y. % | COV | OHV | SV | AV | EpOV % by weight |
| --- | --- | --- | --- | --- | --- | --- | --- | --- | --- | --- | --- | --- |
| 1 | E1 | A1 | 5.0 | — | 180 | 165 | 76.9 | 62 | 32 | 189 | 0.6 | 0.1 |
| 2 | E1 | A1 | 1.0 | — | 180 | 585 | 79.5 | 68 | 33 | 188 | 1.0 | 0.1 |
| 3 | E1 | A2 | 1.0 | 5.0 | 180 | 195 | 77.7 | 62 | 27 | 185 | 1.2 | 0.1 |
| 4 | E1 | A2 | 1.0 | 1.0 | 210 | 420 | 78.1 | 57 | 33 | 188 | 0.6 | 0.1 |
| 5 | E1 | A3 | 1.1 | 4.3 | 180 | 585 | 72.9 | 66 | 19 | 188 | 1.2 | 0.3 |
| 6 | E1 | | | — | 180 | 240 | 78.6 | 63 | 28 | 184 | 1.3 | 0.1 |
| 7 | E1 | A2 | 2.0 | 1.0 | 180 | 420 | 97.0 | 98 | 23 | 3 | 0.2 | 0 |
| 8 | E3 | A1 | 1.0 | — | 200 | 480 | 94.0 | 29 | | 185 | 0.4 | 2.1 |
| 9 | E3 | A3 | 1.2 | 2.3 | 200 | 270 | 94.4 | 31 | | 182 | 0.5 | 1.9 |
| 10 | E4 | A1 | 0.64 | — | 200 | 540 | 96.0 | 21 | | 184 | 0.6 | 3.2 |
| 11 | E4 | A3 | 1.0 | 2.0 | 200 | 510 | 72.8 | 89 | | | | 0.3 |

Legend:
E = educt
A = tetrasubstituted ammonium or phosphonium salt
Y. = Yield, based on epoxide used
COV = carbonyl value
OHV = hydroxyl value

What is claimed is:

1. A process for producing ketones which comprises contacting an epoxide with a catalyst which is comprised of from about 0.5 to about 10 mole % based on said epoxide of a quaternary ammonium or quaternary phosphonium salt.

2. The process of claim 1 wherein said catalyst is further comprised of an alkali metal of alkaline earth metal halide in a molar ratio of said quaternary ammonium of quaternary phosphonium salt to said alkali metal or alkaline earth metal halide of from about 2:1 to about 1:5.

3. The process of claim 2 wherein said catalyst is comprised of a quaternary phosphonium or quaternary ammonium bromide or iodide and sodium iodide.

4. The process of claim 1 wherein said epoxide is an epoxidized monoolefin.

5. The process of claim 1 wherein said epoxide is an epoxidized alkyl alkenyl, aralkyl, or polyol ester of an unsaturated fatty acid.

6. The process of claim 1 wherein said epoxide is an epoxidized alkenyl ester of a saturated fatty acid.

7. The process of claim 1 wherein said quaternary ammonium salt is a quaternary ammonium iodide.

8. The process of claim 1 wherein said catalyst is tetrabutyl phosphonium iodide, tetrabutyl phosphonium bromide, or dimethyl distearyl ammonium chloride.

* * * * *